(12) United States Patent
Melsheimer et al.

(10) Patent No.: US 8,133,190 B2
(45) Date of Patent: Mar. 13, 2012

(54) WELDABLE WIRE GUIDE WITH DISTAL COUPLING TIP

(75) Inventors: Jeffry S. Melsheimer, Springville, IN (US); Brenton S. Krieble, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 17 days.

(21) Appl. No.: 11/763,355

(22) Filed: Jun. 14, 2007

(65) Prior Publication Data

US 2007/0299367 A1 Dec. 27, 2007

Related U.S. Application Data

(60) Provisional application No. 60/815,805, filed on Jun. 22, 2006.

(51) Int. Cl.
*A61B 5/00* (2006.01)
(52) U.S. Cl. ...................................................... 600/585
(58) Field of Classification Search .................... 600/585
See application file for complete search history.

(56) References Cited

U.S. PATENT DOCUMENTS

| | | | |
|---|---|---|---|
| 2,657,691 A | 11/1953 | Nordstrom, Jr. | |
| 3,521,620 A | 7/1970 | Cook | |
| 3,547,103 A | 12/1970 | Cook | |
| 3,656,680 A * | 4/1972 | Nomura | 228/44.3 |
| 3,739,784 A | 6/1973 | Itoh | |
| 3,890,997 A | 6/1975 | Wilson | |
| 4,548,206 A | 10/1985 | Osborne | |
| 4,569,347 A | 2/1986 | Frisbie | |
| 4,601,713 A | 7/1986 | Fuqua | |
| 4,650,472 A | 3/1987 | Bates | |
| 4,665,906 A | 5/1987 | Jervis | |
| 4,824,435 A | 4/1989 | Giesy et al. | |
| 4,921,483 A | 5/1990 | Wijay et al. | |
| 4,925,445 A | 5/1990 | Sakamoto et al. | |
| 4,934,380 A | 6/1990 | De Toledo | |
| 4,984,581 A | 1/1991 | Stice | |
| 5,003,990 A | 4/1991 | Osypka | |
| 5,046,497 A | 9/1991 | Millar | |

(Continued)

FOREIGN PATENT DOCUMENTS

EP 0 436 303 A1 11/1990

(Continued)

OTHER PUBLICATIONS

Nitinol Devices & Components "Joining to Nitinol" 2004. www.nitinol.info/pages/nitinol_facts_5.html.*

(Continued)

*Primary Examiner* — Max Hindenburg
*Assistant Examiner* — Renee Danega
(74) *Attorney, Agent, or Firm* — Brinks Hofer Gilson & Lione

(57) ABSTRACT

A coupling wire guide structured to be slidably coupled to a previously introduced wire guide. The coupling wire guide includes a main body and a coupling tip, the coupling tip having first and second sections. The first section is connected to the main body, while the second section defines an axial passageway having a distal opening and a proximal opening. The axial passageway is sized to receive the previously introduced wire guide therein. Both a distal portion of the main body and the first section are constructed of nitinol, the distal portion and the first section being welded together using the native nitinol material of the distal portion and first section.

27 Claims, 3 Drawing Sheets

U.S. PATENT DOCUMENTS

| | | | |
|---|---|---|---|
| 5,069,226 | A | 12/1991 | Yamauchi et al. |
| 5,105,818 | A | 4/1992 | Christian et al. |
| 5,129,890 | A | 7/1992 | Bates et al. |
| 5,131,407 | A | 7/1992 | Ischinger et al. |
| 5,159,861 | A | 11/1992 | Anderson |
| 5,213,111 | A | 5/1993 | Cook et al. |
| 5,234,003 | A | 8/1993 | Hall |
| 5,242,759 | A | 9/1993 | Hall |
| 5,243,996 | A | 9/1993 | Hall |
| 5,251,640 | A | 10/1993 | Osborne |
| 5,267,958 | A | 12/1993 | Buchbinder et al. |
| 5,306,261 | A | 4/1994 | Alliger et al. |
| 5,318,527 | A | 6/1994 | Hyde et al. |
| 5,325,746 | A | 7/1994 | Anderson |
| 5,328,472 | A | 7/1994 | Steinke et al. |
| 5,328,480 | A | 7/1994 | Milker et al. |
| 5,344,413 | A * | 9/1994 | Allman et al. ............... 604/523 |
| 5,354,257 | A | 10/1994 | Roubin et al. |
| 5,383,853 | A | 1/1995 | Jung et al. |
| 5,402,799 | A | 4/1995 | Colon et al. |
| 5,449,362 | A | 9/1995 | Chaisson et al. |
| 5,456,680 | A | 10/1995 | Taylor et al. |
| 5,488,959 | A * | 2/1996 | Ales ............................. 600/585 |
| 5,597,378 | A | 1/1997 | Jervis |
| 5,667,521 | A | 9/1997 | Keown |
| 5,738,667 | A | 4/1998 | Solar |
| 5,762,070 | A | 6/1998 | Nagamatsu |
| 5,776,079 | A | 7/1998 | Cope et al. |
| 5,776,100 | A | 7/1998 | Forman |
| 5,797,857 | A * | 8/1998 | Obitsu ........................... 600/585 |
| 5,810,876 | A | 9/1998 | Kelleher |
| 5,827,225 | A | 10/1998 | Ma Schwab |
| 5,873,842 | A | 2/1999 | Brennen et al. |
| 5,882,333 | A | 3/1999 | Schaer et al. |
| 5,891,056 | A * | 4/1999 | Ramzipoor ................... 600/585 |
| 5,893,868 | A | 4/1999 | Hanson et al. |
| 5,993,424 | A | 11/1999 | Lorenzo et al. |
| 5,997,526 | A | 12/1999 | Giba et al. |
| 6,007,517 | A | 12/1999 | Anderson |
| 6,139,510 | A | 10/2000 | Palermo |
| 6,217,567 | B1 | 4/2001 | Zadno-Azizi et al. |
| 6,221,066 | B1 | 4/2001 | Ferrera et al. |
| 6,248,092 | B1 | 6/2001 | Miraki et al. |
| 6,254,549 | B1 | 7/2001 | Ramzipoor |
| 6,254,550 | B1 | 7/2001 | McNamara et al. |
| 6,290,693 | B1 | 9/2001 | Jung, Jr. et al. |
| 6,306,141 | B1 | 10/2001 | Jervis |
| 6,309,404 | B1 | 10/2001 | Krzyzanowski |
| 6,348,041 | B1 | 2/2002 | Klint |
| 6,348,045 | B1 | 2/2002 | Malonek et al. |
| 6,383,146 | B1 | 5/2002 | Klint |
| 6,471,697 | B1 | 10/2002 | Lesh |
| 6,475,167 | B1 * | 11/2002 | Fleming et al. ............... 600/585 |
| 6,500,130 | B2 | 12/2002 | Kinsella et al. |
| 6,502,606 | B2 | 1/2003 | Klint |
| 6,517,518 | B2 * | 2/2003 | Nash et al. ............... 604/164.02 |
| 6,530,899 | B1 | 3/2003 | Savage |
| 6,569,151 | B1 | 5/2003 | Nash et al. |
| 6,605,049 | B1 | 8/2003 | Wagner et al. |
| 6,613,002 | B1 | 9/2003 | Clark et al. |
| 6,638,372 | B1 | 10/2003 | Abrams et al. |
| 6,682,608 | B2 | 1/2004 | Abrams et al. |
| 6,805,676 | B2 | 10/2004 | Klint |
| 6,872,192 | B2 | 3/2005 | Nash et al. |
| 7,074,197 | B2 | 7/2006 | Reynolds et al. |
| 7,076,285 | B2 | 7/2006 | Windheuser et al. |
| 7,229,431 | B2 | 6/2007 | Houser et al. |
| 7,527,606 | B2 * | 5/2009 | Oepen ...................... 604/103.04 |
| 2002/0058888 | A1 | 5/2002 | Biagtan et al. |
| 2002/0169457 | A1 | 11/2002 | Quinn |
| 2003/0028127 | A1 | 2/2003 | Balzum et al. |
| 2003/0120208 | A1 | 6/2003 | Houser et al. |
| 2004/0073108 | A1 | 4/2004 | Saeed et al. |
| 2004/0116957 | A1 | 6/2004 | Nishide |
| 2004/0199087 | A1 | 10/2004 | Swain et al. |
| 2004/0215208 | A1 | 10/2004 | Foushee et al. |
| 2005/0027212 | A1 * | 2/2005 | Segner et al. ................. 600/585 |
| 2005/0075647 | A1 | 4/2005 | Walters et al. |
| 2005/0143770 | A1 | 6/2005 | Carter et al. |
| 2005/0148902 | A1 | 7/2005 | Minar et al. |
| 2005/0197663 | A1 | 9/2005 | Soma et al. |
| 2005/0209533 | A1 | 9/2005 | Lorenz |
| 2005/0267442 | A1 | 12/2005 | Von Oepen |
| 2005/0283122 | A1 | 12/2005 | Nordgren |
| 2006/0020256 | A1 | 1/2006 | Bell et al. |
| 2006/0100544 | A1 | 5/2006 | Ayala et al. |
| 2006/0100545 | A1 | 5/2006 | Ayala et al. |
| 2007/0060908 | A1 | 3/2007 | Webster et al. |
| 2007/0014946 | A1 | 6/2007 | Viswanathan et al. |
| 2007/0167065 | A1 | 7/2007 | Melsheimer et al. |
| 2007/0185414 | A1 | 8/2007 | Urbanski et al. |
| 2007/0191790 | A1 | 8/2007 | Eells et al. |

FOREIGN PATENT DOCUMENTS

| | | | |
|---|---|---|---|
| EP | 0 829 269 | A1 | 3/1998 |
| EP | 1 057 500 | A1 | 12/2000 |
| EP | 1 428 546 | A2 | 6/2004 |
| WO | WO 93/14805 | | 8/1993 |
| WO | WO 96/10436 | | 4/1996 |
| WO | WO 99/44510 | | 9/1999 |
| WO | WO 00/74565 | A1 | 12/2000 |
| WO | WO 01/03764 | A1 | 1/2001 |
| WO | WO 02 094364 | A2 | 11/2002 |
| WO | WO2004/033016 | * | 4/2004 |
| WO | WO 2004/049970 | A2 | 6/2004 |
| WO | WO 2004/050161 | A1 | 6/2004 |
| WO | WO 2005/011530 | A1 | 2/2005 |
| WO | WO 2005/011788 | A1 | 2/2005 |
| WO | WO 2005/025660 | A1 | 3/2005 |
| WO | WO 2005/089852 | A1 | 9/2005 |
| WO | WO 2006/039216 | A2 | 4/2006 |
| WO | WO 2007/084474 | A1 | 7/2007 |
| WO | WO 2007/089891 | A3 | 8/2007 |
| WO | WO 2007/089893 | A1 | 8/2007 |

OTHER PUBLICATIONS

Office Action dated Nov. 15, 2007 issued in related U.S. Appl. No. 11/652,430.

The Journal of Invasive Cardiology entitled "Use of a Second Buddy Wire During Percutaneous Coronary Interventions: A Simple Solution for Some Challenging Situations" dated Apr. 25, 2005, pp. 1-8.

International Search Report—PCT/US2006/040843 (Jan. 31, 2007).
International Search Report—PCT/US2007/002743 (Jun. 14, 2007).
International Search Report—PCT/US2007/002741 (Jul. 9, 2007).
International Search Report—PCT/US2006/042184 (Mar. 1, 2007).
International Search Report—PCT/US2007/001066 (Jun. 18, 2007).
International Search Report—PCT/US2007/004827 (Oct. 23, 2007).
International Search Report & Written Opinion (Jan. 3, 2008).
Notification of Transmittal of International Preliminary Report on Patentability (Jan. 10, 2008).
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 30, 2008 U.S. Appl. No. 11/507,805 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).
Office Action Restriction dated Mar. 3, 2008 U.S. Appl. No. 11/507,805 issued in related application.
Office Action Restriction dated Jul. 2, 2008 U.S. Appl. No. 11/699,171 issued in related application.
International Preliminary Report on Patentability—PCT/US2007/002741 (Jun. 25, 2008).
International Preliminary Report on Patentability and Written Opinion (Jul. 24, 2008) PCT/US2007/001066.
Office Action dated Sep. 26, 2008 U.S. Appl. No. 11/706,548 issued in related application.

Office Action dated Oct. 7, 2008 U.S. Appl. No. 11/507,993 issued in related application.
Office Action dated Oct. 15, 2008 U.S. Appl. No. 11/699,174 issued in related application.
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 21, 2008 U.S. Appl. No. 11/549,473 issued in co-pending application.
Office Action dated Nov. 21, 2008 U.S. Appl. No. 11/699,171 issued in co-pending application.
Office Action dated Dec. 11, 2008 U.S. Appl. No. 11/652,430 issued in co-pending application.
Advisory Action dated Jan. 16, 2009 U.S. Appl. No. 11/507,805 issued in co-pending application.
Office Action dated Jun. 4, 2009 U.S. Appl. No. 11/549,473 issued in co-pending application.
Office Action dated Jun. 12, 2009 U.S. Appl. No. 11/699,174 issued in co-pending application.
Advisory Action dated Jun. 25, 2009 U.S. Appl. No. 11/549,481 issued in co-pending application.
Advisory Action dated Jun. 22, 2009 U.S. Appl. No. 11/706,548 issued in co-pending application.
Office Action dated Jun. 23, 2009 U.S. Appl. No. 11/652,430 issued in co-pending application.
Office Action dated Aug. 3, 2009 U.S. Appl. No. 11/699,174 issued in co-pending application.
Office Action dated Sep. 16, 2009 U.S. Appl. No. 11/549,481 issued in co-pending application.
Office Action dated Oct. 14, 2009 U.S. Appl. No. 11/507,805 issued in co-pending application.
Office Action dated Oct. 23, 2009 U.S. Appl. No. 11/706,548 issued in co-pending application.
Office Action dated Dec. 9, 2009 U.S. Appl. No. 11/652,430 issued in co-pending application.
Office Action dated Dec. 14, 2009 U.S. Appl. No. 11/507,993 issued in co-pending application.
Office Action dated Jan. 19, 2010 U.S. Appl. No. 11/699,171 issued in co-pending application.
Office Action dated Apr. 2, 2010 U.S. Appl. No. 11/507,805 issued in co-pending application.
Office Action dated Mar. 12, 2010 U.S. Appl. No. 11/699,174 issued in co-pending application.
Office Action dated Apr. 21, 2010 U.S. Appl. No. 11/706,548 issued in co-pending application.
Notice of Allowance dated Jan. 25, 2010 U.S. Appl. No. 11/549,473 issued in co-pending application.
Notice of Allowance dated Mar. 25, 2010 U.S. Appl. No. 11/549,481 issued in co-pending application.
Notice of Allowance dated May 19, 2010 U.S. Appl. No. 11/699,174 issued in co-pending application.
Notice of Allowance dated May 27, 2010 U.S. Appl. No. 11/699,171 issued in co-pending application.
Notice of Allowance dated Jun. 3, 2010 U.S. Appl. No. 11/652,430 issued in co-pending application.
Office Action (Final) dated Jun. 17, 2010 U.S. Appl. No. 11/507,993 issued in co-pending application.
Advisory Action dated Jun. 17, 2010 U.S. Appl. No. 11/507,805 issued in co-pending application.
Office Action Restriction dated Jun. 23, 2010 U.S. Appl. No. 11/549,466 issued in co-pending application.
Advisory Action dated Jun. 28, 2010 U.S. Appl. No. 11/706,548 issued in co-pending application.
Advisory Action dated Mar. 6, 2009 U.S. Appl. No. 11/652,430 issued in co-pending application.
Office Action dated Mar. 30, 2009 U.S. Appl. No. 11/699,174 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 8, 2009 U.S. Appl. No. 11/699,171 issued in co-pending application.
Office Action dated May 14, 2009 U.S. Appl. No. 11/507,993 issued in coo-pending application.

* cited by examiner

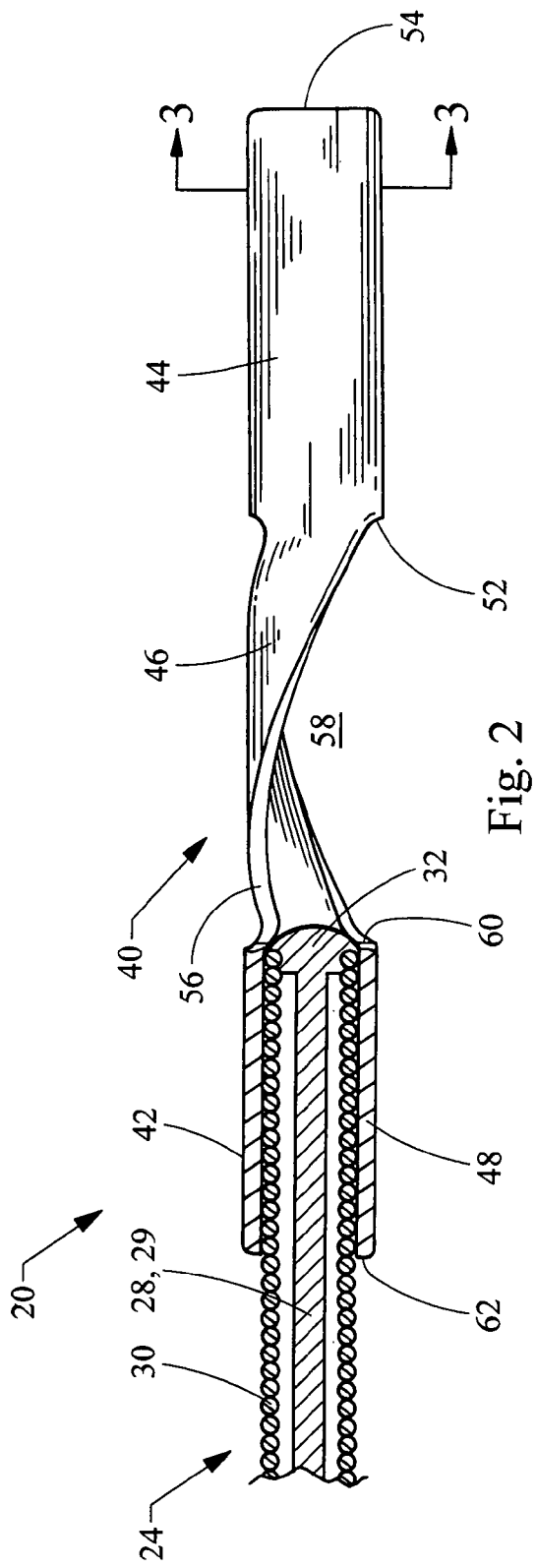
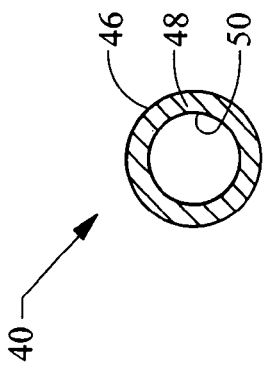
Fig. 2
Fig. 3

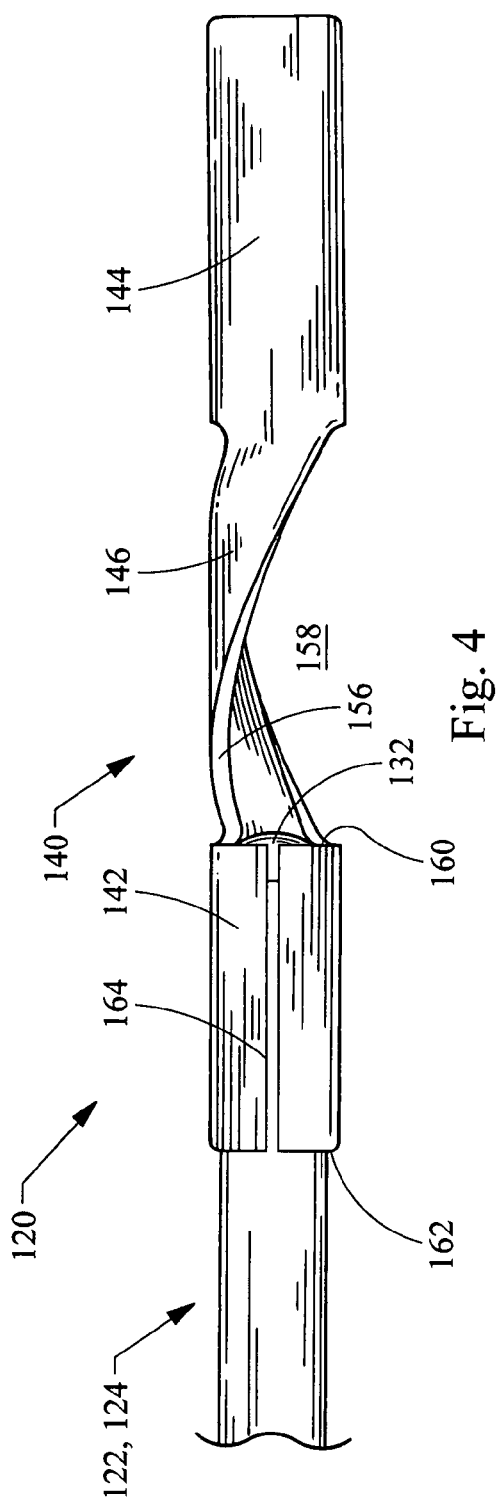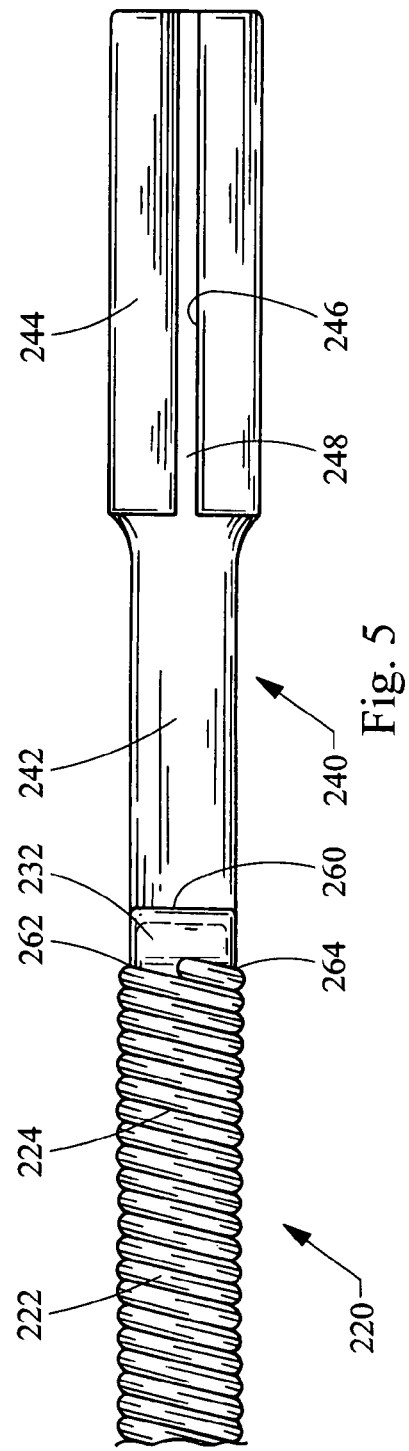

WELDABLE WIRE GUIDE WITH DISTAL COUPLING TIP

CROSS-REFERENCE TO RELATED APPLICATIONS

This application claims the benefit of U.S. Provisional Application Ser. No. 60/815,805 filed on Jun. 22, 2006, entitled "WELDABLE WIRE GUIDE WITH DISTAL COUPLING TIP", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Wire guides are typically used to navigate the vasculature of a patient during intracorporeal procedures. Once the wire guide has been introduced, it may then be used to introduce one or more medical catheter devices. Conventional wire guides are typically 0.014 inches in diameter and have a lubricious coating to enhance wire guide introduction movement. These conventional "floppy" wire guides have sufficient flexibility and torque control for navigation through tortuous vessels. In certain procedures or situations, it is desirable to enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

Several unique supplemental wire guides have been developed which are structured to be slidably coupled to the conventional wire guide (or any previously introduced wire guide) to provide easy and reliable navigation through the vasculature to a position proximate the previously introduced wire guide. These supplemental wire guides are commonly referred to as coupling wire guides or Buddy wires, and exemplary coupling wire guides are disclosed in U.S. patent application Ser. Nos. 11/507,993 filed Aug. 22, 2006; 11/507,805 filed Aug. 22, 2006; 11/699,174 filed Jan. 29, 2007; and 11/699,171 filed Jan. 29, 2007 the disclosures of which are hereby incorporated herein by reference in their entireties. Although other variations exist, many coupling wire guides include a separately formed coupling tip that is connected to a distal portion of a wire guide.

It has been found that the process of joining the coupling tip to the distal portion of the wire guide by soldering (i.e. heating a metal with a lower melting point and causing it to be a structural filler) can have certain drawbacks on small products, such as difficulty in consistent repeatability, difficulty in preparing and cleaning the components to be joined, difficulty in controlling solder flow, difficulty in controlling the heat effected zone, and ultimate corrodibility. Accordingly, there exists a need to provide a coupling wire guide for intracorporeal procedures that overcomes these drawbacks.

BRIEF SUMMARY OF THE INVENTION

The present invention provides a coupling wire guide for intracorporeal procedures that is more easily constructed in a reliable and long-lasting manner. In one embodiment constructed in accordance with the teachings of the present invention, the coupling wire guide generally includes a main body having a distal portion and a coupling tip securely connected to the distal portion of the main body. The coupling tip includes first and second sections. The first section is connected to the main body, while the second section defines an axial passageway having a distal opening and a proximal opening. The axial passageway is sized to receive the previously introduced wire guide therein. Both the distal portion and the first section are constructed of nitinol. The distal portion and the first section are welded together using the native nitinol material of the distal portion and first section. A filler material of nitinol may or may not be used to assist in forming the weld.

Preferably, all of the components of the coupling wire guide are constructed of nitinol, which provides improved control over the characteristics of the coupling wire guide since nitinol can be alloyed, formed, and heat-treated to give all the desired characteristics (e.g. flexibility and resiliency) to the wire guide. According to more detailed aspects of this embodiment, the first section is tubular and disposed over the distal end. The distal portion and the first section are welded together proximate a distal edge of the first section. Additionally, one or more slits may be formed in the first section to provide increased areas for welding. Alternatively, the first section may extend circumferentially less than 360 degrees to define two side edges, and the welding may occur proximate the two side edges and the distal edge. The tip portion may further include a third section interconnecting the first and second sections. The third section preferably includes a strip extending axially and circumferentially to define a complimentary axially and circumferentially extending opening in communication with the proximal opening. In this design, the distal portion and the first section are welded together proximate a distal edge of the first section, as well as proximate a proximal edge of the first section.

According to even further aspects, the main body and its distal portion may take many forms. In one construction, the distal portion includes a wire disposed over a mandrel, the wire and mandrel being constructed of nitinol and welded together using the native nitinol material of the wire and mandrel. An end cap is formed by the weld pool of nitinol, which is formed to have a smooth beveled surface. The distal portion may alternatively comprise a simple mandrel constructed of nitinol, wherein the mandrel and first section are welded together using the native nitinol material of the mandrel and coupling tip. In another form, the main body comprises a mandrel which tapers to include a reduced diameter portion having a wire disposed over the reduced diameter portion in the area of the distal end. Here, the ends of the wire are welded to the reduced diameter portion of the mandrel using the native nitinol material of the wire and mandrel.

A method of forming a coupling wire guide is also provided in accordance with the teachings of the present invention. A main body is provided having a distal portion, the distal portion including a wire disposed over a mandrel, the wire and mandrel constructed of nitinol. A coupling tip is provided having a first section and a second section constructed of nitinol. The first section is structured for connection to the distal portion while the second section defines an axial passageway having distal and proximal openings sized to receive the previously introduced wire guide therein. The ends of the wire are welded to the mandrel using the native nitinol material of the wire and mandrel without filler material. The distal portion of the main body is welded to the first section of the coupling tip using the native nitinol material of the distal portion of the coupling tip without filler material. According to more detailed aspects, the step of welding the distal portion to the first section occurs after the step of welding the ends of the wire to the mandrel.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 2 is an enlarged side view, partially in cross-section, of the coupling wire guide depicted in FIG. 1

FIG. 3 is a cross-sectional view, taken about the line 3-3 in FIG. 2;

FIG. 4 is a cross-sectional view of an alternate embodiment of a coupling wire guide constructed in accordance with the teachings of the present invention; and FIG. 5 is a cross-sectional view of another alternate embodiment of a coupling wire guide constructed in accordance with the teachings of the present invention.

DETAILED DESCRIPTION OF THE INVENTION

Figure 1:
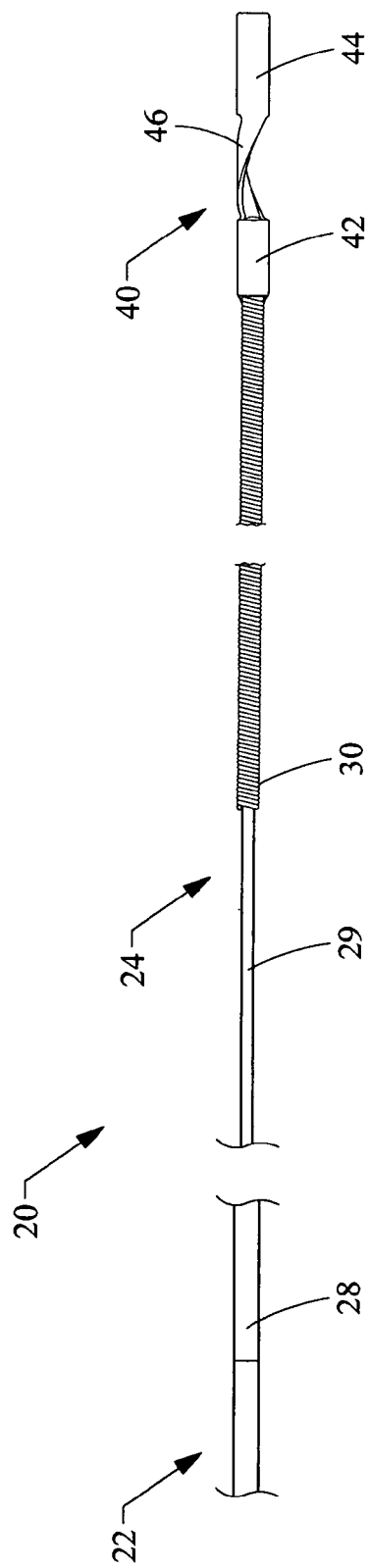
FIG. 1 is a side view of a coupling wire guide constructed in accordance with the teachings of the present invention.

Turning now to the figures, FIGS. 1 to 3 depict a coupling wire guide 20 constructed in accordance with the teachings of the present invention. The coupling wire guide 20 includes a main body 22, which in FIG. 1 has been shown as a solid wire mandrel 28. The main body 22 includes a distal portion 24 that is connected to a coupling tip 40 of the coupling wire guide 20. The coupling tip 40 is uniquely structured for slidably coupling the coupling wire guide 20 to a previously introduced wire guide (not shown), It will be recognized by those skilled in the art that the main body 22 of the coupling wire guide 20 may take numerous forms as many types of wire guides are known in the art, including a solid wire, tubular wires, coiled wires and combinations thereof. As shown in FIGS. 1 and 2, the mandrel 28 tapers in the area of the distal portion 24 to define a reduced diameter portion 29. A wire 30 is disposed over the reduced diameter portion 29, and in particular is in a coiled configuration thereover. As such, the reduced diameter portion 29 of the mandrel 28 serves as a safety wire for the coupling wire guide 20 which is connected to an end cap 32 at the distal free end at the main body 22 and distal portion 24.

As noted above, the coupling tip 40 has been formed at the distal portion 24 of the main body 22 to provide simple and reliable introduction of the coupling wire guide 20 over a previously introduced wire guide. The coupling tip 40 generally comprises a first section 42 and a second section 44. As best seen in FIGS. 2 and 3, the first section 42 is structured as a tubular member 48a that is sized to receive the distal portion 24 of the main body 22. The second section 44 of the coupling tip 40 is also constructed as a tubular member 48b defining an axial passageway 50 therein that is sized and structured to receive the previously introduced wire guide. The second section 44 and its axial passageway 50 also define a proximal opening 52 and a distal opening 54 through which the previously introduced wire guide passes.

A third section 46 is also provided which interconnects the first and second sections 42, 44. The third section 46 generally comprises a strip 56 which serves to provide flexibility to the coupling tip 40. The strip 56 is sized to provide an opening or open area 58 (FIG. 2) for receiving the previously introduced wire guide. The proximal opening 52 is thus in communication with the open area 58 defined by the third section 46 of the coupling tip. To provide the open area 52, the strip 56 extends less than 360 degrees circumferentially, and preferably has a width less than 180 degrees circumferentially. Specifically, the strip 56 follows a curved path between the first and second sections 42, 44, and as shown follows a helical path between the first and second sections 42, 44. In this manner, the strip 56 and third section 46 provide some degree of flexibility to the coupling tip 40, while maintaining a suitable amount of rigidity and securely linking the first and second sections 42, 44.

Uniquely, the main body 22 and coupling tip 40 are constructed of a nickel titanium alloy (nitinol) to provide improved manufacturability of the coupling wire guide 20. Preferably, all of the components of the coupling wire guide 20 are constructed of nitinol, which exhibits the properties of super elasticity and shape memory. Accordingly, all of the components may be heat treated or otherwise formed to provide the desired properties of flexibility and resiliency. In a preferred construction, the mandrel 28 is constructed from a nitinol wire that was formed by drawing through dies and then ground, preferably using a center-less grinding technique. Similarly, the nitinol wire for the outer wire 30 is preferably formed by drawing though dies, and is then pre-formed into a coil shape by pulling the wire across a stress-inducing surface or by winding the nitinol wire around the mandrel 28 and then heat setting the nitinol wire. The coupling tip 40 is preferably constructed from a nitinol cannula which is formed using homogenous technology as described in U.S. Pat. Nos. 4,759,487 and 4,852,790, the disclosures of which are incorporated by reference herein in their entirety. Alternatively, the cannula may be constructed by drawing nitinol stock seamlessly, or by drawing, rolling and welding. The cannula is then laser-cut to shape, electropolished and/or media-blasted and/or abrasive ground to the desired surface finish, and heat-treated to obtain the desired properties.

The nitinol material of the coupling wire guide 20 preferably has an austenitic finish temperature ($A_f$) less than body temperature and in the range of 0 to 35 degrees C. This provides sufficient structural integrity to the wire guide 20 as well as a very fast recovery time from stress-induced deformation. In one preferred construction, $A_f$ is below room temperature and preferably between about 5-10 degrees C., to provide a fully austenitic material both outside and inside the patient. Notwithstanding the temperature range given above, room temperature refers to the typical temperature in an operating room or other environment where intracorporeal procedures are performed, which can vary, as is known in the art. In another preferred construction, $A_f$ is in the range of about 10-35 degrees C., to provide a partially austenitic material outside the patient to improve handling, while fully austenitic inside the patient.

Another benefit of using nitinol is that the various components of the wire guide may be directly welded together since welding nitinol to itself preserves the super elasticity and shape memory of the nitinol material, unlike joining nitinol to the dissimilar metals such as stainless steel (which is also especially difficult due to the formation of brittle intermetallic compounds). Preferably, the welding of the components is performed by fusion welding without a filler material, such as by laser welding or tungsten inert gas (TIG) welding. That is, the native nitinol material of the various components is used during the welding process and fused together. This provides excellent control over the size of the welded components and reduces the package width since a filler material does not need to be accommodated. A filler material may be used to assist in forming the weld, and in this case the filler material is preferably nitinol so as not to affect the properties of the wire guide.

With reference to FIGS. 1 and 2, the outer wire 30 is welded to the reduced diameter portion 29 of the mandrel 28. In particular, a proximal end of the wire is welded directly to the mandrel 28, while the distal end of the wire 30 is connected to the mandrel 28 through the end cap 32, all of which is welded together. Specifically, the end cap 32 is formed by the weld pool of nitinol material from the mandrel 28 and wire 30, the weld pool being cooled and formed to have a smooth beveled surface. Upon formation of the main body 22 and its distal portion 24, the first section 42 of the coupling tip 40 is fitted over the main body 22 and a weld is formed along a proximal edge 62 of the first section 42 between the wire 30 and tubular member 48a of the first section 42. Likewise, by virtue of the third section 46 providing open area 58, another weld may be formed at the distal edge 60 of the first section 42 between the end cap 32, wire 30 and tubular member 48a of the first section 42. Alternatively, the weld at the distal edge 60 may be performed at the same time as welding the madrel 28 and outerwire 30. In this manner, a secure interconnection between the distal portion 24 of the main body 22 and the coupling tip 40 is provided without requiring any filler material. By way of example, successful formation of the wire guide 20 has been accomplished using a mandrel having a 0.0136 inch diameter, an outer wire 30 having a 0.003 inch diameter and laser cutting a cannula 40 which has a 0.004 inch wall thickness. Preferably, the tapered portion 29 of the mandrel 28 extends longitudinally about 6.5 cm, while the wound coil 30 extends longitudinally about 4.5 cm. Also, the first tubular section 42 of the coupling tip 40 overlaps with the distal portion 24 of the main body by about 1.5 mm.

Of course, it will be recognized by those skilled in the art that many different sizes and types of mandrels, wires, and coupling tips may be employed in conjunction with the present invention, including any of those disclosed in co-pending U.S. patent application Ser. Nos. 11/507,993 filed Aug. 22, 2006; 11/507,805 filed Aug. 22, 2006; 11/699,174 filed Jan. 29, 2007; and 11/699,171 filed Jan. 29, 2007. For example, an alternate embodiment of a coupling wire guide 120 has been depicted in FIG. 4 which includes a solid wire main body 122 (also referred to as mandrel 122) and distal portion 124. As with the prior embodiment, a coupling tip 140 is provided which includes first, second and third sections 142, 144, 146. In this embodiment, the first section 142 includes one or more longitudinally extending slits 164. By way of the slits 164, additional area between the mandrel 122 and first section 142 is provided for welding. As such, the first section 142 and mandrel 122 may be welded together along the slits 164 as well as around the distal and proximal edges 160, 162 of the first section 142 of the coupling tip 140. The slits may extend in directions other than longitudinally, for example circumferentially or combinations thereof (i.e. angled or curved).

Turning to FIG. 5, yet another embodiment of a coupling wire guide 220 has been depicted. As with the embodiment of FIGS. 1-3, the main body 222 includes a coiled wire which forms a distal portion 224 having an end cap 232. The coupling tip 240 includes a first section 242 and a second section 244. The second section 244 provides a "side-loading" function through the provision of an axial slot 246 which provides access to the coupling passageway 248. It will be recognized that the slot 246 could extend diagonally as well. In this embodiment, the first section 242 is formed as an annular strip which extends less than 360 degrees. Accordingly, the first section 242 defines two side edges 262, 264 which extend longitudinally and provide an additional area for welding the distal portion 224 of the main body to the first section 242 of the coupling tip 240. As with the previous embodiments, a weld may also be formed at the distal end 260 of the main body 222 proximate the end cap 232. Thus, the welding uses the native material of the distal portion's outer wire 230 and the first section 242 of the coupling tip 240.

Accordingly, it will be recognized by those skilled in the art that a coupling wire guide is provided in accordance with the teachings of the present invention which is more easily constructed in a reliable and long-lasting manner, while providing improved control over the properties of the coupling wire guide. Likewise, the outer diameter of the coupling wire guide may be reduced by using the native nitinol material of the wire guide components for forming the welds.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide in intracorporeal procedures, the coupling wire guide comprising:
   a main body having a distal portion with a coiled outer wire; and
   a coupling tip positioned at the distal portion of the main body, the coupling tip including a first section connected to the main body; a second section defining an axial passageway and a longitudinal axis having a distal opening and a proximal opening, the axial passageway sized to receive the previously introduced wire guide therein; and a third section interconnecting the first and second sections, the third section including a strip extending axially and circumferentially that defines a complementary axially and circumferentially extending opening in communication with the proximal opening, the axially and circumferentially extending opening being coaxial with the distal portion of the main body, the strip being of a semi-annular cross-sectional shape and following a curved helical path extending around the longitudinal axis, the helical path making less than one turn;
   wherein both the distal portion and the first section are constructed of nitinol, the distal portion and the first section being welded together using the native nitinol material of the distal portion and first section.

2. The coupling wire guide of claim 1, wherein the first section is tubular and disposed over the distal end, and wherein the distal portion and the first section are welded together proximate a distal edge of the first section.

3. The coupling wire guide of claim 1, wherein the first section extends circumferentially less that 360 degrees to define two side edges, and wherein the distal portion and first section are welded together along the two side edges.

4. The coupling wire guide of claim 1, wherein the distal portion and first section are welded together proximate a distal edge of the first section.

5. The coupling wire guide of claim 4, wherein the first section is tubular and disposed over the distal end.

6. The coupling wire guide of claim 1, wherein the first section is tubular and includes a longitudinal slit providing an open area for welding the distal portion and first section.

7. The coupling wire guide of claim 1, wherein the distal portion includes a wire disposed over a mandrel, the wire and mandrel constructed of nitinol and welded together at the distal portion using the native nitinol material of the wire and mandrel.

8. The coupling wire guide of claim 7, further comprising an end cap that is formed through welding of the native nitinol material of the wire and mandrel.

9. The coupling wire guide of claim 7, wherein the mandrel has a diameter of about 0.0136 inches.

10. The coupling wire guide of claim 7, wherein the wire has a diameter of about 0.003 inches.

11. The coupling wire guide of claim 7, wherein the nitinol material of the main body and coupling tip has an $A_f$ in the range of about 0 to 35 degrees Celsius.

12. The coupling wire guide of claim 11, wherein $A_f$ is below room temperature.

13. The coupling wire guide of claim 11, wherein $A_f$ is above room temperature and below body temperature.

14. The coupling wire guide of claim 1, wherein the distal portion comprises a mandrel constructed of nitinol, and wherein the mandrel and first section welded together using the native nitinol material of the mandrel and coupling tip.

15. The coupling wire guide of claim 1, wherein the main body comprises a mandrel, the mandrel including a reduced diameter portion having a wire disposed thereover in the area of the distal end.

16. The coupling wire guide of claim 15, wherein ends of the wire are welded to the reduced diameter portion of the mandrel using the native nitinol material of the wire and mandrel.

17. The coupling wire guide of claim 1, wherein the first section of the coupling tip is tubular and has a thickness of about 0.004 inches.

18. The coupling wire guide of claim 1, wherein the first section of the coupling tip extends axially about 1.5 mm.

19. The coupling wire guide of claim 1 wherein the axially and circumferentially extending opening is also coaxial with the axial passageway of the second section.

20. The coupling wire guide of claim 1 wherein a natural unbiased configuration of the strip follows the helical path making less than one turn.

21. The coupling wire guide of claim 1 wherein the second section of the coupling tip is a solid tubular section.

22. A method of forming a coupling wire guide capable of being slidably coupled to a previously introduced wire guide, the method comprising the steps of:
  providing a main body having a distal end, the distal portion including a wire disposed over a mandrel, the wire and mandrel constructed of nitinol;
  providing a coupling tip having a first section structured for connection to the distal portion; a second section defining an axial passageway and a longitudinal axis, a distal opening and a proximal opening, the axial passageway sized to receive the previously introduced wire guide therein the coupling tip constructed of nitinol; and a third section interconnecting the first and second sections, the third section including a strip extending axially and circumferentially that defines a complementary axially and circumferentially extending opening in communication with the proximal opening, the axially and circumferentially extending opening being coaxial with the distal portion of the main body, the strip having a semi-annular cross-sectional shape and following a curved helical path around the longitudinal axis, the curved helical path spanning less than 360 degrees;
  welding ends of the wire to the mandrel using the native nitinol material of the wire and mandrel; and
  welding the distal portion of the main body to the first section of the coupling tip using the native nitinol material of the distal portion and the coupling tip.

23. The method of claim 22, wherein the step of welding the distal portion to the first section occurs after the step of welding the ends of the wire to the mandrel.

24. The method of claim 22, wherein the welding steps do not include the any filler material between the welded structures.

25. The method of claim 22, wherein the two welding steps are performed simultaneously.

26. A coupling wire guide for coupling to a previously introduced wire guide in intracorporeal procedures, the coupling wire guide comprising:
  a main body having a distal portion; and
  a coupling tip positioned at the distal portion of the main body, the coupling tip including a first section connected to the main body, a second section defining an axial passageway having a distal opening and a proximal opening and a third section interconnecting the first and second sections, the axial passageway sized to receive the previously introduced wire guide therein; and
  wherein the first section is tubular and includes a longitudinal slit providing an open area for welding the distal portion of the main body and first section;
  wherein the third section includes a strip extending axially and circumferentially that defines a complementary axially and circumferentially extending opening in communication with the proximal opening, the axially and circumferentially extending opening being coaxial with the distal portion of the main body, the strip extending less than 360 degrees circumferentially and having a circumferential width of less than 180 degrees, and wherein the distal portion and first section are welded together proximate the third section;
  wherein both the distal portion and the first section are constructed of nitinol, the distal portion and the first section being welded together using the native nitinol material of the distal portion and first section.

27. The coupling wire guide of claim 26 wherein the axially and circumferentially extending opening spans about 180 degrees or greater.

* * * * *